US008712131B2

(12) United States Patent
Pfister et al.

(10) Patent No.: US 8,712,131 B2
(45) Date of Patent: Apr. 29, 2014

(54) DETERMINATION METHOD FOR A REINITIALIZATION OF A TEMPORAL SEQUENCE OF FLUOROSCOPIC IMAGES OF AN EXAMINATION REGION OF AN EXAMINATION OBJECT

(75) Inventors: Marcus Pfister, Bubenreuth (DE); Thomas Redel, Poxdorf (DE)

(73) Assignee: Siemens Aktiengesellschaft, München (DE)

( * ) Notice: Subject to any disclaimer, the term of this patent is extended or adjusted under 35 U.S.C. 154(b) by 964 days.

(21) Appl. No.: 12/825,369

(22) Filed: Jun. 29, 2010

(65) Prior Publication Data

US 2010/0329526 A1     Dec. 30, 2010

(30) Foreign Application Priority Data

Jun. 30, 2009  (DE) .......................... 10 2009 031 139

(51) Int. Cl.
G06K 9/00          (2006.01)
(52) U.S. Cl.
USPC .......................................................... 382/130
(58) Field of Classification Search
None
See application file for complete search history.

(56) References Cited

U.S. PATENT DOCUMENTS

| 7,729,525 | B2 * | 6/2010 | Camus et al. | 382/130 |
| 2007/0041625 | A1 | 2/2007 | Camus et al. | |
| 2008/0033285 | A1 * | 2/2008 | Camus et al. | 600/425 |
| 2008/0051648 | A1 | 2/2008 | Suri et al. | |

FOREIGN PATENT DOCUMENTS

| DE | 102005039189 A1 | 2/2007 |
| DE | 102005062446 A1 | 7/2007 |
| DE | 102007024450 A1 | 11/2008 |

OTHER PUBLICATIONS

Endovaskuläre Behandlung zerebraler AV-Malformationen AWMF online / Arbeitsgemeinschaft der Wissenschaftlichen Medizinischen Fachgesellschaften http://www.uni-duesseldorf.de/awmf/ll/047-014.htm.
Kontinuierlich aktualisierte Roadmaps, z.B. Embolisationen, 2008E13098DE = 2009J06853 (Sperrveröffentlichung).

* cited by examiner

*Primary Examiner* — Robert Morgan
*Assistant Examiner* — Michael Tomaszewski

(57) ABSTRACT

A determination method for reinitialization of a temporal sequence of fluoroscopic images of an examination region of an examination object is provided. The examination region comprises a vascular system including arteries and/or veins. An acquisition time is assigned to each of the images representing a given distribution of a substance in the examination region at the acquisition time. A computer receives the temporal sequence of the images, determines an evaluation image corresponding spatially on a pixel-by-pixel basis to the images, and calculates a differential value between a pixel of the evaluation image at a time and a pixel at a preceding time during a time characteristic of the sequence. A reinitialization of the temporal sequence of the images is performed at a specific time and thereafter the determination method is started over and/or repeated. The specific time is determined as a function of at least one previously calculated differential value.

12 Claims, 4 Drawing Sheets

Live images (fluoro)

Subtracted images (roadmaps)

DETERMINATION METHOD FOR A REINITIALIZATION OF A TEMPORAL SEQUENCE OF FLUOROSCOPIC IMAGES OF AN EXAMINATION REGION OF AN EXAMINATION OBJECT

CROSS REFERENCE TO RELATED APPLICATIONS

This application claims priority of German application No. 10 2009 031 139.4 filed Jun. 30, 2009, which is incorporated by reference herein in its entirety.

FIELD OF THE INVENTION

The present invention relates to a determination method for a reinitialization of a temporal sequence of fluoroscopic images of an examination region of an examination object. The invention also relates to devices corresponding hereto.

BACKGROUND OF THE INVENTION

During an intervention on an angiography system, real-time images are acquired with the aid of fluoroscopic X-ray transillumination, e.g. for the purpose of navigating the instruments (e.g. in head or heart). A frequently performed intervention on such a system is the embolization of tumors or arteriovenous malformations (AVMs), as indicated in FIG. 1.

Arteriovenous malformations (AVMs) are congenital malformations of the vascular system, frequently malformations of the vascular system of the central nervous system, the brain or the visceral cranium. In a malformation of said kind a direct connection exists between the arteries and the veins of the vascular system. This means that between the arteries and the veins there are no capillary vessels in which the actual exchange of oxygen and nutrients between the blood and the tissue takes place. One consequence of this is that the affected tissue region is not supplied with blood. Another consequence is that the pressure in the veins increases, causing them to widen and possibly leading to hemorrhaging. In this event brain hemorrhages in particular are potentially very critical.

Three methods for treating AVMs are currently available, these also being used in combination in most cases. Specifically, these are neurosurgical operations, radiotherapy and endovascular therapies. Irrespective of the way in which an AVM is treated, a precise knowledge of the location, shape and characteristics of the AVM, as well as of the detailed blood flow conditions, is essential for the planning and execution of the treatment. Both morphological information (location, size and type of the blood vessels) as well as functional time-dependent information (flow conditions) are therefore necessary.

For diagnostic purposes, computed tomography and magnetic resonance tomography in particular are possible as non-invasive imaging modalities. In addition an angiography is often performed in the interests of precise clarification and detailed treatment planning. In this case C-arm-based, temporally static and three-dimensionally spatially resolved imaging or two-dimensionally spatially resolved and one-dimensionally temporally resolved imaging are available as alternatives.

The interventional endovascular therapy takes place using fluoroscopy in the angiography laboratory. Angiographic scenes (in particular DSA scenes) through the corresponding vascular region are produced for planning and monitoring purposes. The scenes can be recorded on monoplane systems, though biplane systems are better suited, with two scenes being recorded in parallel from different angulations. The evaluation can be carried out for each of the two scenes.

It is important in this case to track the continuous progress of the embolization, in particular in order to prevent the reflux of embolic agent into unaffected vessels. Typically, such procedures are observed with the aid of subtracted recorded images in which only the differences from a specific mask image are to be seen, as shown for example in FIG. 1 in image B). An advantage in this case is that anatomical backgrounds are "subtracted away". The progression of the embolization can also be monitored more effectively since following a reinitialization of the mask the embolic agent that has accumulated up to that point is also no longer visible in the (subtracted) subsequent recorded images.

On the other hand this can be a disadvantage, since following a reinitialization of the mask the physician can no longer recognize the already embolized regions. It is also of advantage for the physician not to see the newly embolized regions as a "growing black area". It is important for the physician to be able to assess the progression, i.e. to recognize at a glance which region has been embolized before the others or, as the case may be, where newly injected embolic agent is currently accumulating.

Usually it is possible to employ what is referred to as a roadmap technique. To put it differently, a native mask is recorded which is subtracted from the following live X-ray images, i.e. during the intervention, in order to make changes visible thereby. If it is intended to study a continuous process, said mask has constantly to be reinitialized manually.

A determination method for a color-coded first evaluation image is known from DE 10 2007 024 450 A1. A computer receives a temporal sequence of X-ray images, to each of which an acquisition time is assigned and each of which represents a given contrast agent distribution in the examination region of an examination object at the respective acquisition time. The examination region comprises a vascular system and tissue supplied with blood via the vascular system. The computer in each case determines a characteristic value for each pixel of an evaluation image which uniquely corresponds to one of the blood vessels of the vascular system (single vessel pixel) for each of the X-ray images on the basis of the data values of the pixels of the respective X-ray image which lie in a first evaluation core that is defined by means of the respective single vessel pixel and is spatially uniform for all the X-ray images. The X-ray images and the first evaluation image correspond spatially to one another on a pixel-by-pixel basis. Based on the variation with time of the characteristic values of the respective single vessel pixel the computer determines for each single vessel pixel a characteristic time for the arrival time of the contrast agent at the respective single vessel pixel. In addition it assigns a color property that is characteristic of the respective characteristic time to each single vessel pixel and a color property that is independent of the characteristic time to every other pixel. The computer outputs the evaluation image color-coded in this way to a user. In this case a specific color coding scheme is proposed for each mask reinitialization.

There is a problem here with regard to the manual reinitialization of the masks, since the physician does not want to have constantly to perform the initialization himself/herself.

It is possible to perform a continuous reinitialization. An updated mask is automatically calculated continuously from the stream of native fluoroscopic images. For this purpose it is possible, for example, always to combine M consecutive images or to merge the images from the live stream continuously to form a mask. Said mask is further more subtracted from the live images, with the updated mask being used every K images or seconds (selectable by the user). As a result only the changes compared with the last mask image are ever visible, which means that the process can be tracked continuously.

In this case the selection of the most suitable time for a reinitialization is critical, since a reinitialization of the mask during a phase of major image changes can generate artifacts in the following recorded subtraction images.

SUMMARY OF THE INVENTION

The object of the present invention is to create ways by means of which an automatic reinitialization of the masks can be improved.

This object is achieved by means of the features recited in the independent claims. Advantageous developments are characterized in the dependent claims.

The present invention achieves said object inter alia by finding an "optimal" initialization instant at a time in which only a "minimal image change" is present in the sequences. In order to measure the "minimal image change" use is preferably made of an image (motion) energy of the sequence with moving objects which can be represented by means of an image motion energy function or curve.

The present invention relates to a determination method for a reinitialization of a temporal sequence of fluoroscopic images of an examination region of an examination object,
   wherein the examination region comprises a vascular system,
   wherein the vascular system includes arteries and/or veins as blood vessels,
   wherein each of the fluoroscopic images is assigned an acquisition time (t) and each of the fluoroscopic images represents a given distribution of a substance in the examination region at the respective acquisition time (t), and
   wherein a computer receives the temporal sequence of fluoroscopic images and determines at least one evaluation image which is to be output to a user and which corresponds spatially to the fluoroscopic images on a pixel-by-pixel basis.

According to the invention the method can be performed by a computer. The computer can output at least one color-coded evaluation image to a user as the result of the performed method.

BRIEF DESCRIPTION OF THE DRAWINGS

Further advantages, details and developments of the invention will emerge from the following description of exemplary embodiments taken in conjunction with the exemplary schematic drawings, in which.

DETAILED DESCRIPTION OF THE INVENTION

Figure 1:
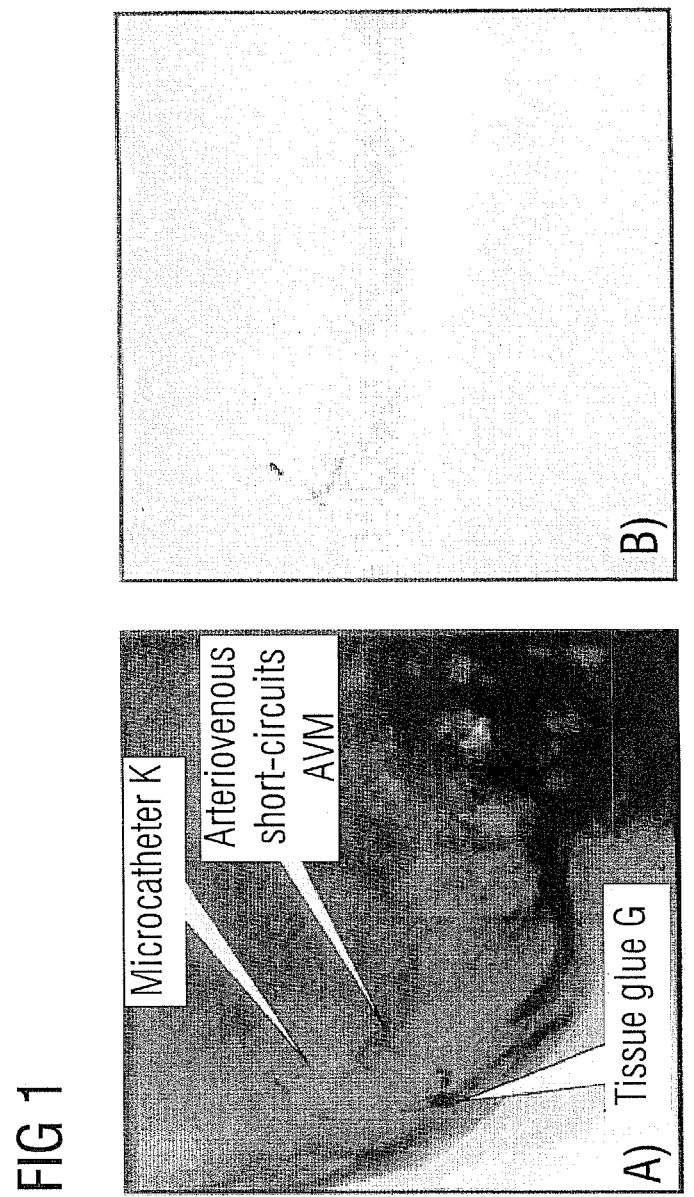
FIG. 1 shows a native fluoroscopic image A) and an image B) subtracted therefrom

Arteriovenous malformations AVM are indicated in FIG. 1A). Tissue glue G (e.g. Onyx) is introduced via a microcatheter K which is selectively inserted into the artery that is to be treated in order to occlude the arteriovenous short-circuits or malformations. A) shows the native fluoroscopic image, while FIG. 1B) shows the correspondingly subtracted image (roadmap) on which only the differences compared with a specific mask image can be seen. Roadmap images largely consist of "neutral" background (namely the parts in which the live image (image recorded during the intervention) is identical to the mask and which are therefore "subtracted away") and the changes in the live image compared with the mask which stand out as dark (see image B). In certain circumstances artifacts can stand out as white spots. The invention is not limited to the embodiment variant relating to an embolization. The invention can also be applied in an analogous manner to "roadmap" images in connection with administration of a contrast agent—such as is known e.g. from the publication DE 10 2007 024 450 A1 cited in the introduction.

Figure 4:
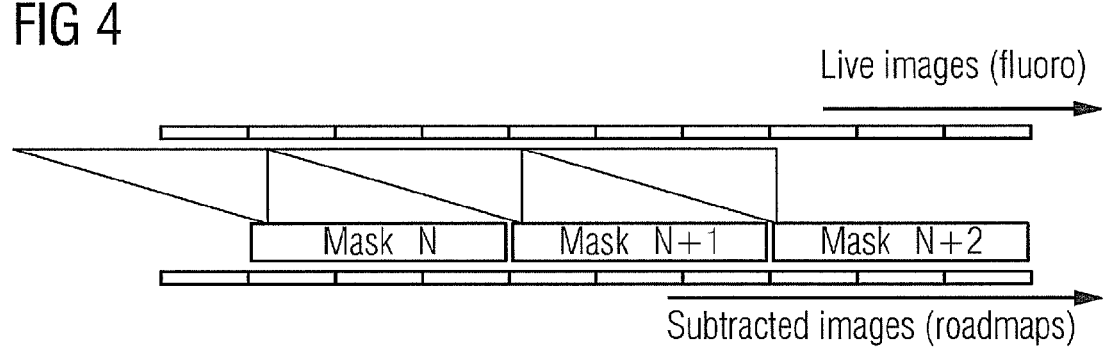
FIG. 4 shows a possible approach as to how M images can be combined to form a mask from the stream of native fluoroscopic images.

FIG. 4 show a possibility of how M images (three in this case) can be combined to form a mask from the stream of native fluoroscopic images. Said mask is subtracted from the following images of the live stream or sequence in order that an updated mask can be calculated automatically and continuously from the stream of native fluoroscopic images.

A new mask for the following subtraction images is to be selected automatically from the stream of native fluoroscopic images at specific times. In principle the user should be able to select an "optimal" minimum run time for a mask before the expiration of which no reinitialization will take place. The object according to the invention is to find an "optimal" initialization time after said time has elapsed. It is favorable to select an instant of "minimal image change" in order to avoid artifact formations in the following subtraction images.

Because the roadmap images essentially consist of neutral background and the changes compared with the last mask (black), the individual roadmaps can be readily segmented and for example the changes over time combined in a color-coded manner into a single image. Where appropriate the grayscale values of a pixel or a group of pixels can also be evaluated given constant recording parameters. If this changes, a propagation of the embolic agent in the X-ray beam direction is given. This can be evaluated for all pixels and visualized in color- or brightness-coded form.

At the present time the roadmap is mostly obtained from a DSA (Digital Subtraction Angiography) acquisition. A variant can therefore consist in overlaying the above-described detected changes on an original DSA roadmap.

A further aid for the physician is to overlay the catheter, since oftentimes the distal end of the catheter is no longer visible during or toward the end of the intervention.

For this purpose the catheter can be segmented in an early acquisition/roadmap and continuously superimposed on the live images.

The object according to the invention is to find an "optimal" initialization time instant after said time period has elapsed. It is favorable to choose a moment of "minimal image change" in order to avoid artifact formations in the following subtraction images.

For finding an "optimal" initialization instant the concept of the image (motion) energy of a sequence with moving objects shall be defined first. If an image sequence contains moving structures, the difference between two succeeding images can count as a metric for said movement. For the purpose of the evaluation the curve representing the motion energy can also be smoothed. If the movement between the times t1 and t2 is slow (see FIG. 2 A)), this difference is small, and hence so is the corresponding energy. If rapid movements occur (see FIG. 2 B)), the difference is commensurately greater. Plotted over the complete sequence, an energy curve is produced as shown e.g. in FIG. 2 C). High energy values occur in an embolization sequence whenever a drop of the embolic agent detaches itself from the catheter and flows with the blood flow into the AVM. These times should be avoided for the reinitialization.

As a basic principle care will be taken to ensure that a certain time elapses between two reinitializations.

Figure 2:
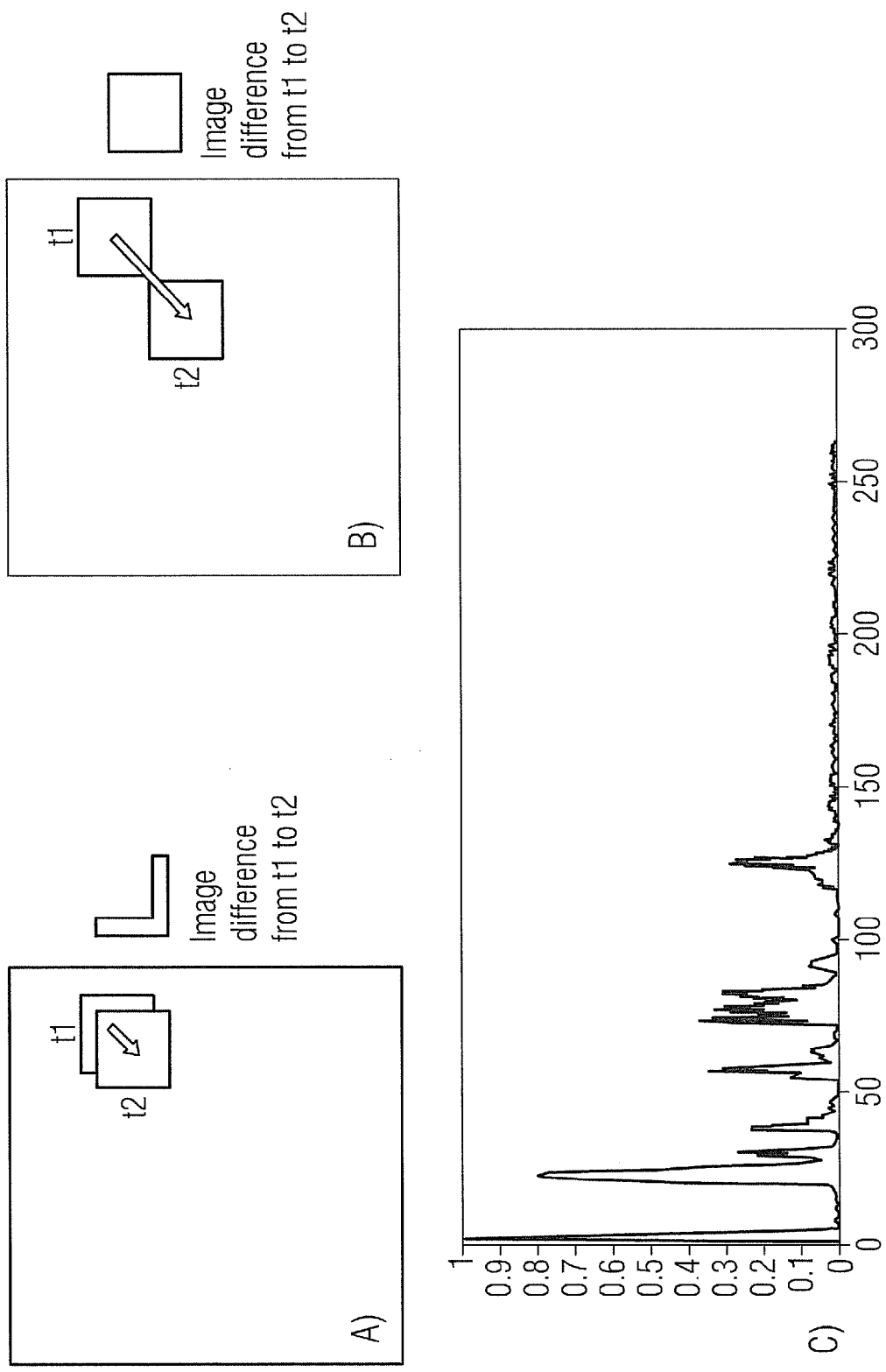
FIG. 2 shows in image A) and B) an exemplary image sequence of moving structures, wherein a metric for the difference in these movements is defined, and in image C) an image energy curve for the image sequence.
Figure 3:
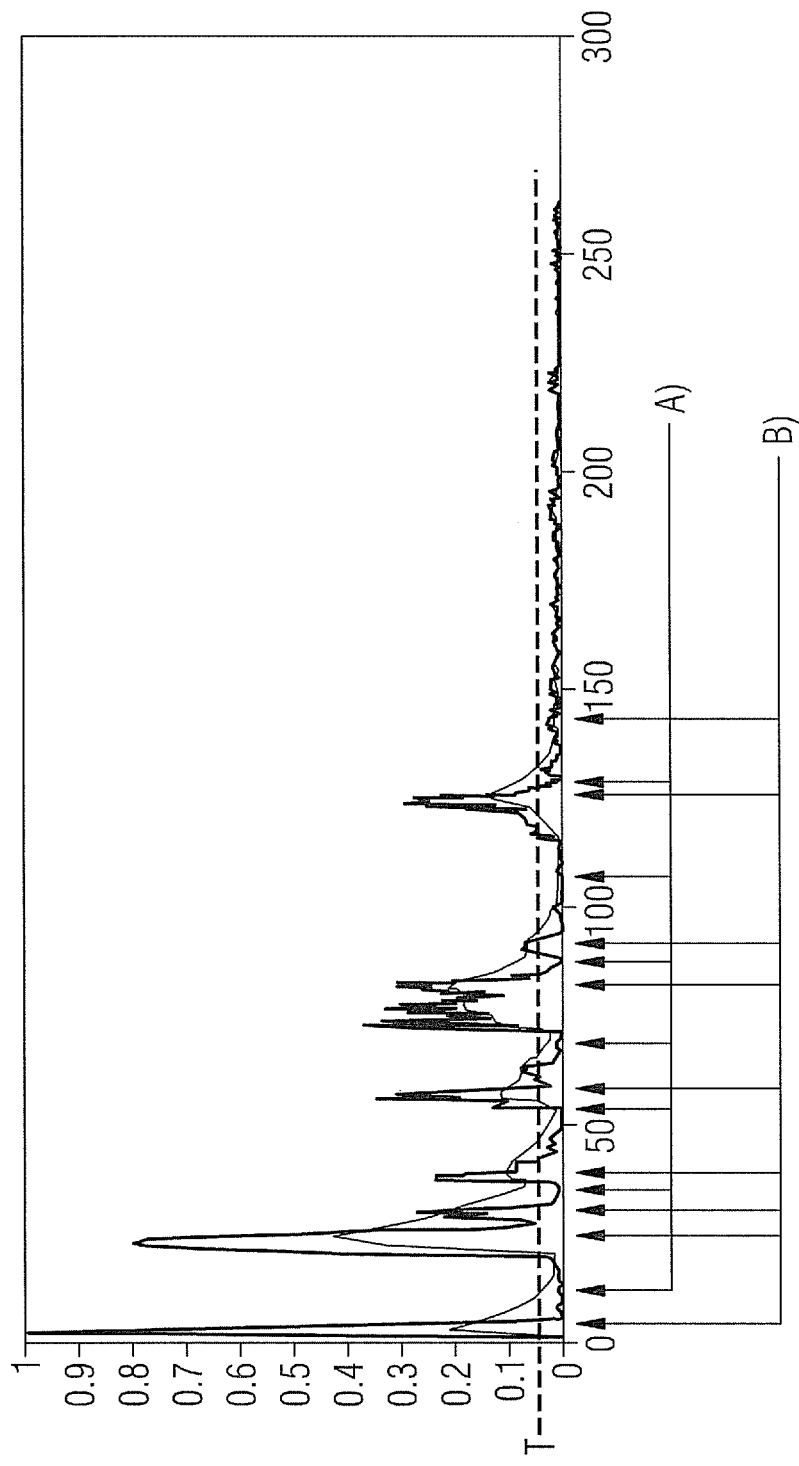
FIG. 3 shows by way of example potential initialization times according to A) and B) which result from the energy curve from FIG. 2 C)

The energy curve—as shown e.g. in FIG. 2 C)—can be referred to for the purpose of selecting these times. Potential initialization times—as indicated e.g. in FIG. 3 by A) and B)—are produced whenever the energy curve exhibits minima. Two selection options are illustrated:

In image A) the roadmap can be reinitialized whenever the image energy (curve printed in bold) falls below a specific value T. Specifying T can be a problem here, particularly in the case of small image changes.

B) shows possible initialization points as sections of the energy curve having a running mean of the same (curve printed in non-bold). Choosing the smoothing factor can be a problem here.

A further possibility is e.g. a quasi-analytical curve discussion of the energy curve in order to determine the minima.

Fluoroscopy or sequence pauses are considered exceptions in this case, e.g. a reinitialization can additionally be performed after an interruption in recording.

Figure 5:
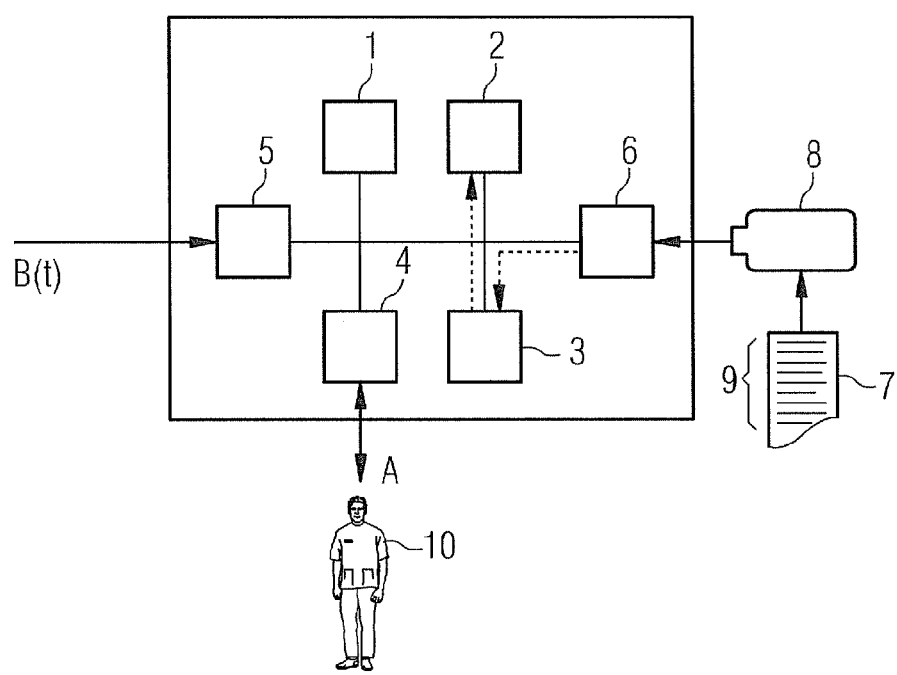
FIG. 5 is a block diagram of an evaluation arrangement.

According to FIG. 5 such a computer has typical components 1 to 6. In particular the computer has a microprocessor 1, a random access memory (RAM) 2, a mass storage device 3 (a hard disk, for example), a user interface 4, a data interface 5 and a programming interface 6. The components 1 to 6 are embodied in the usual way and interact with one another in the usual way. Thus, for example, the user interface 4 can include typical input and output devices such as, for example, a keyboard, a mouse, a visual display unit, etc. The data interface 5 can be an internet or a LAN interface, for example, or a USB interface. An embodiment as a drive for a replaceable medium (a CD-ROM or DVD, for example) is possible. Similar embodiments are possible for the programming interface 6. Where appropriate the data interface 5 and the programming interface 6 can be combined to form a common interface.

The computer is supplied with a computer program 7 via the programming interface 6. For example, a data medium 8 on which the computer program 7 is stored in machine-readable form can be connected to the computer. The computer program 7 is thereupon read out from the data medium 8 and copied into the mass storage device 3 of the computer, i.e. is also stored there.

The computer program 7 contains machine code 9, i.e. program instructions, which can be executed by the computer directly and immediately. The computer program 7 can be launched by a user 10 by means of typical input commands (a double mouse click, for example). When the computer program 7 is launched, it is loaded into the computer's random access memory 2 and executed by the computer. The execution of the computer program 7 by the computer causes the computer to perform a determination method that has been described in detail hereintofore in conjunction with the further figures.

The computer can determine an evaluation image A on the basis of a sequence of fluoroscopy or X-ray images B and their acquisition times t. The computer can output the color-coded evaluation image A to the user 10.

In a further embodiment variant the computer can output a further color-coded evaluation image to the user simultaneously with the color-coded evaluation image.

The computer can receive a further temporal sequence of fluoroscopic images and determine the color-coded further evaluation image on the basis of the further temporal sequence of fluoroscopic images in an analogous manner to the first-mentioned color-coded evaluation image.

The difference compared with the approach described in the foregoing consists in the fact that although the further sequence of X-ray images are X-ray images of the same examination object and of the same examination region of the examination object and were also recorded using the same recording geometry, the further sequence was acquired at a different time than the acquisition of the first-mentioned sequence.

For example, the computer can represent the two evaluation images side by side or one overlaid on the other. It is also possible for the computer to determine where the two evaluation images deviate from one another and to output the differential image to the user 10.

The present invention has many advantages. In particular it is possible to observe continuous processes (e.g. embolizations) and reinitialize corresponding masks at optimal times. Therefore the reinitialization of the masks no longer has to be performed manually by the user. Furthermore artifacts in the live images are avoided by means of the method according to the invention.

Generally the above-described method can also be used for other vascular malformations (e.g. fistulae, aneurysms, stenoses, etc.), as well as for neoplastic changes in the brain, but also other regions of the body.

The foregoing description serves solely to explain the present invention. The scope of protection of the present invention, on the other hand, is to be determined solely by the attached claims.

The invention claimed is:

1. A method for reinitializing a temporal sequence of fluoroscopic images of an examination region of an examination object, wherein the examination region comprises a vascular system including arteries and/or veins as blood vessels, comprising:
   assigning an acquisition time to each of the fluoroscopic images representing a given distribution of a substance in the examination region at the acquisition time;
   receiving the temporal sequence of the fluoroscopic images by a computer;
   determining an evaluation image based on differences from a mask image to be output to a user corresponding spatially on a pixel-by-pixel basis to the fluoroscopic images by the computer;
   calculating a differential value between a pixel of the evaluation image at a time t and a pixel at a preceding time t−1 by the computer, the differential value providing a metric for image change;
   determining a specific time t' for reinitializing the mask image for the temporal sequence of the fluoroscopic images as a function of the differential value by the computer, wherein the specific time t' corresponds with a time in which a minimal image change is present in the temporal sequence; and
   reinitializing the mask image for the temporal sequence of the fluoroscopic images at the specific time t' by the computer.

2. The method as claimed in claim 1, wherein the specific time t' is determined when the differential value is below a predefined threshold value.

3. The method as claimed in claim 1, wherein the differential values is calculated via a motion energy curve.

4. The method as claimed in claim 1, wherein the specific time t' is determined when a minimum of a motion energy curve can be determined.

5. The method as claimed in claim 1, wherein the specific time t' is determined when a running mean is calculated over a motion energy curve and an agreement can be established between the motion energy curve and the running mean.

6. The method as claimed in claim 1, wherein the evaluation image is presented visually for the user on a display device of the computer.

7. The method as claimed in claim 1, wherein a characteristic color property for the differential value is assigned to each pixel of the evaluation image.

8. The method as claimed in claim 7, wherein a grayscale image of the vascular system on the evaluation image is overlaid with the evaluation image being assigned with the characteristic color property.

9. The method as claimed in claim 8, wherein a grayscale value of the each pixel is incorporated in the characteristic color property as a brightness value.

10. The method as claimed in claim 1, wherein the user selects an evaluation area of the evaluation image and the computer performs the method only within the evaluation area.

11. A computer program stored on a non-transitory computer readable medium and executable by a computer for reinitializing a temporal sequence of fluoroscopic images of an examination region of an examination object, wherein the examination region comprises a vascular system including arteries and/or veins as blood vessels, comprising:
a machine code for:
assigning an acquisition time to each of the fluoroscopic images representing a given distribution of a substance in the examination region at the acquisition time;
receiving the temporal sequence of the fluoroscopic images;
determining an evaluation image based on differences from a mask image to be output to a user corresponding spatially on a pixel-by-pixel basis to the fluoroscopic images;
calculating a differential value between a pixel of the evaluation image at a time t and a pixel at a preceding time t−1, the differential value providing a metric for image change;
determining a specific time t' for reinitializing the mask image for the temporal sequence of the fluoroscopic images as a function of the differential value, wherein the specific time t' corresponds with a time in which a minimal image change is present in the temporal sequence; and
reinitializing the mask image for the temporal sequence of the fluoroscopic images at the specific time t'.

12. A computer for reinitializing a temporal sequence of fluoroscopic images of an examination region of an examination object, wherein the examination region comprises a vascular system including arteries and/or veins as blood vessels, comprising:
a storage device that stores a computer program for:
assigning an acquisition time to each of the fluoroscopic images representing a given distribution of a substance in the examination region at the acquisition time;
receiving the temporal sequence of the fluoroscopic images;
determining an evaluation image based on differences from a mask image to be output to a user corresponding spatially on a pixel-by-pixel basis to the fluoroscopic images;
calculating a differential value between a pixel of the evaluation image at a time t and a pixel at a preceding time t−1, the differential value providing a metric for image change;
determining a specific time t' for reinitializing the mask image for the temporal sequence of the fluoroscopic images as a function of the differential value, wherein the specific time t' corresponds with a time in which a minimal image change is present in the temporal sequence; and
reinitializing the mask image for the temporal sequence of the fluoroscopic images at the specific time t'.

* * * * *